United States Patent [19]

Hasegawa et al.

[11] 4,301,162

[45] Nov. 17, 1981

[54] ANTIBACTERIAL AND ANTIFUNGAL COMPOSITION

[75] Inventors: Masayasu Hasegawa, Kyoto; Hideo Nishikawa, Ibaraki; Kayoko Yoshida, Takatsuki, all of Japan

[73] Assignee: Nippon Gohsei Kagaku Kogyo Kabushiki Kaisha, Osaka, Japan

[21] Appl. No.: 163,161

[22] Filed: Jun. 26, 1980

Related U.S. Application Data

[63] Continuation-in-part of Ser. No. 58,446, Jul. 18, 1979, Pat. No. 4,242,336.

[51] Int. Cl.$^3$ .................... A01N 37/06; A01N 43/02; A01N 43/40; A01N 55/02
[52] U.S. Cl. .................................... 424/263; 424/245; 424/246; 424/279; 424/314; 424/319
[58] Field of Search ....................... 424/279, 263, 245

[56] References Cited

PUBLICATIONS

The Merck Index 9th Ed. (1976), pp. 135, 279, 375, 644, 950, 994, 1126, 1184, 1197 & 1198.
Kuehle et al., C.A., vol. 62, No. 4, 3973 (1965).
The Merck Index 9th ed. (1976), p. 1037.

*Primary Examiner*—Allen J. Robinson
*Attorney, Agent, or Firm*—Armstrong, Nikaido, Marmelstein & Kubovcik

[57] ABSTRACT

An antibacterial and antifungal composition comprising a mixture of (A) at least one member selected from the group consisting of dehydroacetic acid and its alkali metal salts and (B) at least one member selected from the group consisting of 2-pyridinethiol 1-oxide and its salts. The antibacterial and antifungal effects can be synergistically increased when the component (A) is employed in combination with the component (B).

2 Claims, No Drawings

ANTIBACTERIAL AND ANTIFUNGAL COMPOSITION

CROSS-REFERENCE TO RELATED APPLICATION

This application is a continuation-in-part of applicants' copending application Ser. No. 58,446 filed on July 18, 1979 now U.S. Pat. No. 4,242,336, issued 12/30/80.

BACKGROUND OF THE INVENTION

The present invention relates to a composition useful as antibacterial and antifungal agent, and more particularly to an antibacterial and antifungal composition mainly containing dehydroacetic acid, sorbic acid or their alkali metal salts.

It is well known that dehydroacetic acid, sorbic acid and their alkali metal salts are useful as antibacterial and antifungal agents. The toxicity of these antibacterial and antifungal agents is so low that their addition to foods is permitted, and they are agents of very high safety. Therefore, if these agents are usable in any fields such as general industrial products and agricultural products, to say nothing of foods, the usefulness of these agents becomes very great. However, the antibacterial antifungal effects thereof are not always satisfactory in the application to industrial products such as paints, sizing agents and adhesives.

SUMMARY OF THE INVENTION

In accordance with the present invention, there is provided an antibacterial and antifungal composition comprising a mixture of (A) 60% to 99.5% by weight of at least one member selected from the group consisting of dehydroacetic acid and its alkali metal salts and (B) 0.5% to 40% by weight of at least one member selected from the group consisting of 2-pyridinethiol 1-oxide and its salts.

The synergistic effect on the antibacterial and antifungal properties is very remarkable, when the component (A) is employed in combination with a definite amount of the component (B), and the composition of the invention can be availably employed as antibacterial and antifungal agents in various industrial products and agricultural products.

DETAILED DESCRIPTION

There are employed, as the component (A) of the composition of the invention, dehydroacetic acid, sorbic acid and their alkali metal salts such as sodium dehydroacetate, potassium dehydroacetate, sodium sorbate and potassium sorbate. These compounds may be employed alone or in admixture thereof.

In the present invention, the component (A) is employed in combination with component (B) selected from the group consisting of higher alkyl-di(aminoethyl)-glycines, their salts, 2-pyridinethiol 1-oxide and its salts, and tetrahydro-3,5-dimethyl-2H-1,3,5,-thiadiazine-2-thione.

The higher alkyl-di(aminoethyl)glycines employed in the present invention are compounds having the following general formula:

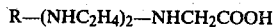

wherein R is an alkyl group having 8 to 16 carbon atoms. Examples of these alkyldi(aminoethyl)glycines are octyl-, nonyl-, decyl-, undecyl-, dodecyl-, tridecyl-, tetradecyl-, pentadecyl- and hexadecyl-di(aminoethyl)glycines, and dodecyl-, tridecyl- and tetradecyl-di(aminoethyl)glycines are preferably employed. The alkyldi(aminoethyl)glycines are also employed in the form of their salts with organic or inorganic acids such as hydrochloric acid, sulfuric acid and acetic acid.

2-Pyridinethiol 1-oxide employed as the component (B) is a compound shown by the following formula:

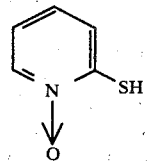

There are also employed in the invention metal salts of 2-pyridinethiol 1-oxide such as the sodium, salt and the zinc salt, shown by the following formulas:

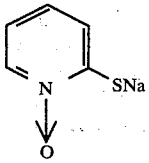 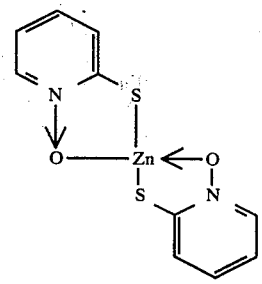

Tetrahydro-3,5-dimethyl-2H-1,3,5-thiadiazine-2-thione employed as the component (B) is a compound shown by the following formula:

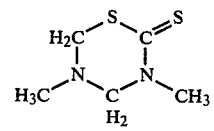

The component (A) should be employed in an amount of 60% to 99.5% by weight and the component (B) should be employed in an amount of 0.5% to 40% by weight, respectively based on the weight of the mixture of the components (A) and (B), since the particularly remarkable synergistic effect can be obtained. As stated before, the feature of the present invention is that the antibacterial and antifungal effects of dehydroacetic acid, sorbic acid or their alkali metal salts can be remarkably increased, when they are employed in combination with a definite amount of the component (B). Although the compounds employed as the component (B) are known as antibacterial and antifungal agents, it has now been found that synergistic antibacterial and antifungal effect unexpected from a single use of various known antibacterial and antifungal agents can be obtained, when among known antibacterial and antifungal agents the component (A) and the component (B) are particularly combined. When the proportion of the component (B) is less than 0.5% by weight, sufficient synergistic effect cannot be obtained. Also, even if the component (B) is employed in an amount of more than 40% by weight, the synergitic effect is not increased. Further, the compounds employed as the component (B) are relatively expensive and also the toxicity is higher than the component (A) and, therefore, the use of the component (B) in an amount of more than 40% by weight not only be uneconomical, but also may impair the low toxicity by which the feature of the composition of the present invention is characterized.

In the present invention, the mixture of only the components (A) and (B) may be availably employed as an antibacterial and antifungal composition, and also auxiliary agents such as other bactericides, other fugicides, surface active agents, chelate compounds, e.g. ethylenediaminetetraacetic acid chelate, citric acid and polyphosphoric acid, and fillers such as clay, talc, diatomaceous earth and bentonite may be further incorporated in the above mixture. It is needless to say that the weight ratio of component (A) to component (B) must be in the range of 99.5/0.5 to 60/40 in the composition containing the auxiliary agents or fillers.

The composition of the present invention is applicable to any industrial products and agricultural products which require the annihilation or the prevention of propagation of bacteria and fungi, such as paints, sizing agents, petroleum products, plastic moldings, fibers, leathers, woods, paper goods, cosmetics, pharmaceuticals, medical appliances, industrial equipments, building material (putties, fiber boards, particle boards, gypsum boards), fruits, grains and vegetables, and food products.

The amount of the composition added to the above products varies depending on the kind of the products to be added. In general, sufficient antibacterial and antifungal effects are obtained, when the mixture of the components (A) and (B) is contained in the products in an amount of 50 to 8,000 p.p.m. When the amount is less than 50 p.p.m., no effective antibacterial and antifungal effects are obtained. Also, the addition in an amount of more than 8,000 p.p.m. is uneconomical.

The present invention is more particularly described and explained by means of the following Examples, in which all % are by weight unless otherwise noted.

EXAMPLE 1

A liquid culture medium of pH 7.0 containing 1% of peptone, 1% of meat extract and 0.1% of sodium chloride was prepared and sterilized, and 10 ml. portions thereof were poured into L-shaped tubes. After adding a prescribed amount of an antibacterial, antifungal composition consisting of the components (A) and (B) as shown in Table 1 to each tube, 0.1 ml. (number of cells: $5 \times 10^4$ cells/ml.) of an aqueous suspension of bacteria as shown in Table 1 was added to each tube. The thus prepared culture liquor contained $5 \times 10^2$ cells per milliliter. The culture was carried out at 37° C. for 48 hours with reciprocal shaking, and the state of the growth of bacteria was then observed by measuring the number of cells in 1 ml. of the culture liquor.

The results are shown in Table 1.

TABLE 1

| Bacteria | Antibacterial, antifungal composition Component (A) | Component (B) | (A)/(B) by weight | Amount of composition added (p.p.m.) | Number of cells (cells/ml.) |
|---|---|---|---|---|---|
| Bacillus subtilis | Sodium dehydroacetate | Dodecyldi(aminoethyl)-glycine | 95/5 | 500 | $5 \times 10$ |
| | | | 95/5 | 1000 | 0 |
| | | | 90/10 | 500 | $4 \times 10$ |
| | | | 90/10 | 1000 | 0 |
| | | | 80/20 | 500 | 0 |
| | | | 60/40 | 500 | 0 |
| | | | 100/0 | 500 | $23 \times 10^7$ |
| | | | 100/0 | 1000 | $9 \times 10^4$ |
| | | | 0/100 | 25 | $34 \times 10^8$ |
| | | | 0/100 | 50 | $17 \times 10^6$ |
| | | | 0/100 | 100 | $18 \times 10^4$ |
| | | | 0/100 | 200 | $3 \times 10$ |
| Bacillus subtilis | Potassium sorbate | Dodecyldi(aminoethyl)-glycine | 95/5 | 500 | $8 \times 10$ |
| | | | 95/5 | 1000 | 0 |
| | | | 90/10 | 500 | $3 \times 10$ |
| | | | 90/10 | 1000 | 0 |
| | | | 80/20 | 500 | 0 |
| | | | 60/40 | 500 | 0 |
| | | | 100/0 | 500 | $7 \times 10^8$ |
| | | | 100/0 | 1000 | $5 \times 10^7$ |
| | | | 0/100 | 25 | $34 \times 10^8$ |
| | | | 0/100 | 50 | $17 \times 10^6$ |
| | | | 0/100 | 100 | $18 \times 10^4$ |
| | | | 0/100 | 200 | $3 \times 10$ |
| Bacillus subtilis | Dehydroacetic acid | Sodium salt of 2-pyridinethiol 1-oxide | 99.5/0.5 | 500 | $10 \times 10$ |
| | | | 99.5/0.5 | 1000 | $3 \times 10$ |
| | | | 99/1 | 500 | $5 \times 10$ |
| | | | 99/1 | 1000 | $2 \times 10$ |
| | | | 95/5 | 500 | $2 \times 10$ |
| | | | 95/5 | 1000 | 0 |
| | | | 90/10 | 500 | $1 \times 10$ |
| | | | 90/10 | 1000 | 0 |
| | | | 80/20 | 500 | 0 |
| | | | 60/40 | 500 | 0 |
| | | | 100/0 | 500 | $8 \times 10^5$ |
| | | | 100/0 | 1000 | $12 \times 10^3$ |
| | | | 0/100 | 5 | $50 \times 10^5$ |
| | | | 0/100 | 10 | $35 \times 10^5$ |
| | | | 0/100 | 25 | $12 \times 10^5$ |
| | | | 0/100 | 50 | $20 \times 10^3$ |
| | | | 0/100 | 100 | $30 \times 10^2$ |

TABLE 1-continued

| Bacteria | Antibacterial, antifungal composition Component (A) | Component (B) | (A)/(B) by weight | Amount of composition added (p.p.m.) | Number of cells (cells/ml.) |
|---|---|---|---|---|---|
| Bacillus subtilis | Sorbic acid | Sodium salt of 2-pyridinethiol 1-oxide | 0/100 | 200 | $5 \times 10$ |
| | | | 95/5 | 500 | 9 |
| | | | 95/5 | 1000 | 0 |
| | | | 90/10 | 500 | 8 |
| | | | 90/10 | 1000 | 0 |
| | | | 80/20 | 500 | 5 |
| | | | 80/20 | 1000 | 0 |
| | | | 60/40 | 500 | 0 |
| | | | 100/0 | 500 | $13 \times 10^6$ |
| | | | 100/0 | 1000 | $18 \times 10^4$ |
| | | | 0/100 | 25 | $12 \times 10^5$ |
| | | | 0/100 | 50 | $20 \times 10^3$ |
| | | | 0/100 | 100 | $30 \times 10^2$ |
| | | | 0/100 | 200 | $5 \times 10$ |
| Escherichia coli | Dehydroacetic acid | Tetrahydro-3,5-dimethyl-2H-1,3,5-thiadiazine-2-thione | 95/5 | 500 | 13 |
| | | | 95/5 | 1000 | 0 |
| | | | 90/10 | 500 | 0 |
| | | | 90/10 | 1000 | 0 |
| | | | 80/20 | 500 | 0 |
| | | | 60/40 | 500 | 0 |
| | | | 100/0 | 500 | $13 \times 10^8$ |
| | | | 100/0 | 1000 | $31 \times 10^6$ |
| | | | 0/100 | 25 | $38 \times 10^5$ |
| | | | 0/100 | 50 | $6 \times 10^3$ |
| | | | 0/100 | 100 | $16 \times 10^2$ |
| | | | 0/100 | 200 | $9 \times 10$ |
| Escherichia coli | Sorbic acid | Tetrahydro-3,5-dimethyl-2H-1,3,5-thiadiazine-2-thione | 95/5 | 500 | 15 |
| | | | 95/5 | 1000 | 0 |
| | | | 90/10 | 500 | 8 |
| | | | 90/10 | 1000 | 0 |
| | | | 80/20 | 500 | 0 |
| | | | 60/40 | 500 | 0 |
| | | | 100/0 | 500 | $8 \times 10^6$ |
| | | | 100/0 | 1000 | $7 \times 10^5$ |
| | | | 0/100 | 25 | $38 \times 10^5$ |
| | | | 0/100 | 50 | $6 \times 10^3$ |
| | | | 0/100 | 100 | $16 \times 10^2$ |
| | | | 0/100 | 200 | $9 \times 10$ |
| Staphylococcus aureus | Dehydroacetic acid | Tetradecyldi(aminoethyl)glycine | 95/5 | 500 | $9 \times 10$ |
| | | | 95/5 | 1000 | 0 |
| | | | 90/10 | 500 | $4 \times 10$ |
| | | | 90/10 | 1000 | 0 |
| | | | 80/20 | 500 | $5 \times 10$ |
| | | | 80/20 | 1000 | 0 |
| | | | 60/40 | 500 | 0 |
| | | | 100/0 | 500 | $22 \times 10^5$ |
| | | | 100/0 | 1000 | $6 \times 10^3$ |
| | | | 0/100 | 25 | $19 \times 10^8$ |
| | | | 0/100 | 50 | $17 \times 10^6$ |
| | | | 0/100 | 100 | $18 \times 10^4$ |
| | | | 0/100 | 200 | $7 \times 10$ |
| Staphylococcus aureus | Sorbic acid | Tetradecyldi(aminoethyl)glycine | 95/5 | 500 | $15 \times 10$ |
| | | | 95/5 | 1000 | 0 |
| | | | 90/10 | 500 | $13 \times 10$ |
| | | | 90/10 | 1000 | 0 |
| | | | 80/20 | 500 | $5 \times 10$ |
| | | | 80/20 | 1000 | 0 |
| | | | 60/40 | 500 | 0 |
| | | | 100/0 | 500 | $21 \times 10^6$ |
| | | | 100/0 | 1000 | $5 \times 10^3$ |
| | | | 0/100 | 25 | $19 \times 10^8$ |
| | | | 0/100 | 50 | $17 \times 10^6$ |
| | | | 0/100 | 100 | $18 \times 10^4$ |
| | | | 0/100 | 200 | $7 \times 10$ |
| Pseudomonas aeruginosa | Sodium dehydroacetate | Sodium salt of 2-pyridinethiol 1-oxide | 99.5/0.5 | 500 | 30 |
| | | | 99.5/0.5 | 1000 | 15 |
| | | | 99/1 | 500 | 20 |
| | | | 99/1 | 1000 | 0 |
| | | | 95/5 | 500 | 9 |
| | | | 95/5 | 1000 | 0 |
| | | | 90/10 | 500 | 4 |
| | | | 90/10 | 1000 | 0 |
| | | | 80/20 | 500 | 0 |
| | | | 60/40 | 500 | 0 |
| | | | 100/0 | 500 | $15 \times 10^8$ |
| | | | 100/0 | 1000 | $2 \times 10^7$ |

TABLE 1-continued

| Bacteria | Antibacterial, antifungal composition | | Amount of composition added (p.p.m.) | Number of cells (cells/ml.) |
|---|---|---|---|---|---|
| | Component (A) | Component (B) | (A)/(B) by weight | | |
| | | | 0/100 | 5 | $30 \times 10^6$ |
| | | | 0/100 | 10 | $25 \times 10^6$ |
| | | | 0/100 | 25 | $3 \times 10^6$ |
| | | | 0/100 | 50 | $6 \times 10^4$ |
| | | | 0/100 | 100 | $9 \times 10^3$ |
| | | | 0/100 | 200 | $4 \times 10$ |
| Pseudomonas aeruginosa | Potassium sorbate | Sodium salt of 2-pyridinethiol 1-oxide | 95/5 | 500 | $11 \times 10$ |
| | | | 95/5 | 1000 | 0 |
| | | | 90/10 | 500 | $6 \times 10$ |
| | | | 90/10 | 1000 | 0 |
| | | | 80/20 | 500 | $1 \times 10$ |
| | | | 80/20 | 1000 | 0 |
| | | | 60/40 | 500 | 0 |
| | | | 100/0 | 500 | $15 \times 10^{10}$ |
| | | | 100/0 | 1000 | $7 \times 10^8$ |
| | | | 0/100 | 25 | $3 \times 10^6$ |
| | | | 0/100 | 50 | $6 \times 10^4$ |
| | | | 0/100 | 100 | $9 \times 10^3$ |
| | | | 0/100 | 200 | $4 \times 10$ |
| Pseudomonas aeruginosa | Sodium dehydroacetate | Tetrahydro-3,5-dimethyl-2H-1,3,5-thiadiazine-2-thione | 95/5 | 500 | 3 |
| | | | 95/5 | 1000 | 0 |
| | | | 90/10 | 500 | 0 |
| | | | 80/20 | 500 | 0 |
| | | | 60/40 | 500 | 0 |
| | | | 100/0 | 500 | $15 \times 10^8$ |
| | | | 100/0 | 1000 | $2 \times 10^7$ |
| | | | 0/100 | 25 | $7 \times 10^5$ |
| | | | 0/100 | 50 | $38 \times 10^3$ |
| | | | 0/100 | 100 | $6 \times 10^2$ |
| | | | 0/100 | 200 | $3 \times 10$ |
| Pseudomonas aeruginosa | Potassium sorbate | Tetrahydro-3,5-dimethyl-2H-1,3,5-thiadiazine-2-thione | 95/5 | 500 | 8 |
| | | | 95/5 | 1000 | 0 |
| | | | 90/10 | 500 | 0 |
| | | | 80/20 | 500 | 0 |
| | | | 60/40 | 500 | 0 |
| | | | 100/0 | 500 | $15 \times 10^{10}$ |
| | | | 100/0 | 1000 | $7 \times 10^8$ |
| | | | 0/100 | 25 | $7 \times 10^5$ |
| | | | 0/100 | 50 | $38 \times 10^3$ |
| | | | 0/100 | 100 | $6 \times 10^2$ |
| | | | 0/100 | 200 | $3 \times 10$ |

EXAMPLE 2

A 5% aqueous solution of starch was prepared and sterilized, and 100 ml. portions thereof were poured into 200 ml. bottles. After adding a prescribed amount of an antibacterial, antifungal composition consisting of the components (A) and (B) as shown in Table 2 to each bottle and thoroughly agitating, 1 ml. (number of fungi: $5 \times 10^6$ fungi/ml.) of an aqueous suspension of fungi as shown in Table 2 was added to each bottle and was agitated again. The thus prepared aqueous solution contained $5 \times 10^4$ fungi per gram. The bottles were then sealed and allowed to stand at 30° C. for a week. The state of the growth of fungi was observed by measuring the number of fungi in 1 g. of the aqueous solution.

The results are shown in Table 2.

TABLE 2

| Fungi | Antibacterial, antifungal composition | | Amount of composition added (p.p.m.) | Number of fungi (fungi/g.) |
|---|---|---|---|---|---|
| | Component (A) | Component (B) | (A)/(B) by weight | | |
| Aspergillus niger | Sodium dehydroacetate | Dodecyldi(aminoethyl)-glycine | 95/5 | 500 | 5 |
| | | | 95/5 | 1000 | 0 |
| | | | 90/10 | 500 | 3 |
| | | | 90/10 | 1000 | 0 |
| | | | 80/20 | 500 | 0 |
| | | | 60/40 | 500 | 0 |
| | | | 100/0 | 500 | $18 \times 10^7$ |
| | | | 100/0 | 1000 | $30 \times 10^4$ |
| | | | 0/100 | 25 | $8 \times 10^8$ |
| | | | 0/100 | 50 | $13 \times 10^6$ |
| | | | 0/100 | 100 | $28 \times 10^5$ |
| | | | 0/100 | 200 | $7 \times 10^2$ |
| Aspergillus niger | Potassium sorbate | Dodecyldi(aminoethyl)-glycine | 95/5 | 500 | $4 \times 10$ |
| | | | 95/5 | 1000 | 0 |
| | | | 90/10 | 500 | $2 \times 10$ |
| | | | 90/10 | 1000 | 0 |

TABLE 2-continued

| Fungi | Antibacterial, antifungal composition | | (A)/(B) by weight | Amount of composition added (p.p.m.) | Number of fungi (fungi/g.) |
|---|---|---|---|---|---|
| | Component (A) | Component (B) | | | |
| | | | 80/20 | 500 | 7 |
| | | | 80/20 | 1000 | 0 |
| | | | 60/40 | 500 | 0 |
| | | | 100/0 | 500 | $7 \times 10^{10}$ |
| | | | 100/0 | 1000 | $37 \times 10^8$ |
| | | | 0/100 | 25 | $8 \times 10^8$ |
| | | | 0/100 | 50 | $13 \times 10^6$ |
| | | | 0/100 | 100 | $28 \times 10^5$ |
| | | | 0/100 | 200 | $7 \times 10^2$ |
| Aspergillus niger | Sodium dehydroacetate | Sodium salt of 2-pyridinethiol 1-oxide | 99.5/0.5 | 500 | 10 |
| | | | 99.5/0.5 | 1000 | 2 |
| | | | 99/1 | 500 | 5 |
| | | | 99/1 | 1000 | 0 |
| | | | 95/5 | 500 | 7 |
| | | | 95/5 | 1000 | 0 |
| | | | 90/10 | 500 | 0 |
| | | | 80/20 | 500 | 0 |
| | | | 60/40 | 500 | 0 |
| | | | 100/0 | 500 | $18 \times 10^7$ |
| | | | 100/0 | 1000 | $30 \times 10^4$ |
| | | | 0/100 | 5 | $15 \times 10^7$ |
| | | | 0/100 | 10 | $30 \times 10^5$ |
| | | | 0/100 | 25 | $28 \times 10^4$ |
| | | | 0/100 | 50 | $19 \times 10^3$ |
| | | | 0/100 | 100 | $13 \times 10^2$ |
| | | | 0/100 | 200 | $5 \times 10$ |
| Aspergillus niger | Potassium sorbate | Sodium salt of 2-pyridinethiol 1-oxide | 95/5 | 500 | 9 |
| | | | 95/5 | 1000 | 0 |
| | | | 90/10 | 500 | 5 |
| | | | 90/10 | 1000 | 0 |
| | | | 80/20 | 500 | 0 |
| | | | 60/40 | 500 | 0 |
| | | | 100/0 | 500 | $7 \times 10^{10}$ |
| | | | 100/0 | 1000 | $37 \times 10^8$ |
| | | | 0/100 | 25 | $28 \times 10^4$ |
| | | | 0/100 | 50 | $19 \times 10^3$ |
| | | | 0/100 | 100 | $13 \times 10^2$ |
| | | | 0/100 | 200 | $5 \times 10$ |
| Aspergillus niger | Sodium dehydroacetate | Tetrahydro-3,5-dimethyl-2H-1,3,5-thiadiazine-2-thione | 95/5 | 500 | $6 \times 10$ |
| | | | 95/5 | 1000 | 0 |
| | | | 90/10 | 500 | $5 \times 10$ |
| | | | 90/10 | 1000 | 0 |
| | | | 80/20 | 500 | 0 |
| | | | 60/40 | 500 | 0 |
| | | | 100/0 | 500 | $18 \times 10^7$ |
| | | | 100/0 | 1000 | $30 \times 10^4$ |
| | | | 0/100 | 25 | $7 \times 10^4$ |
| | | | 0/100 | 50 | $12 \times 10^3$ |
| | | | 0/100 | 100 | $19 \times 10^2$ |
| | | | 0/100 | 200 | $3 \times 10$ |
| Aspergillus niger | Potassium sorbate | Tetrahydro-3,5-dimethyl-2H-1,3,5-thiadiazine-2-thione | 95/5 | 500 | $5 \times 10$ |
| | | | 95/5 | 1000 | 0 |
| | | | 90/10 | 500 | $2 \times 10$ |
| | | | 90/10 | 1000 | 0 |
| | | | 80/20 | 500 | 0 |
| | | | 60/40 | 500 | 0 |
| | | | 100/0 | 500 | $7 \times 10^7$ |
| | | | 100/0 | 1000 | $37 \times 10^8$ |
| | | | 0/100 | 25 | $7 \times 10^4$ |
| | | | 0/100 | 50 | $12 \times 10^3$ |
| | | | 0/100 | 100 | $19 \times 10^2$ |
| | | | 0/100 | 200 | $3 \times 10$ |
| Penicillium citrinum | Dehydroacetic acid | Tetradecyldi(aminoethyl)-glycine | 95/5 | 500 | 10 |
| | | | 95/5 | 1000 | 0 |
| | | | 90/10 | 500 | 4 |
| | | | 90/10 | 1000 | 0 |
| | | | 80/20 | 500 | 0 |
| | | | 60/40 | 500 | 0 |
| | | | 100/0 | 500 | $1 \times 10^5$ |
| | | | 100/0 | 1000 | $17 \times 10^3$ |
| | | | 0/100 | 25 | $5 \times 10^7$ |
| | | | 0/100 | 50 | $8 \times 10^5$ |
| | | | 0/100 | 100 | $30 \times 10^3$ |
| | | | 0/100 | 200 | $6 \times 10$ |
| Penicillium | Sorbic acid | Tetradecyldi(aminoethyl)- | | | |

TABLE 2-continued

| Fungi | Antibacterial, antifungal composition Component (A) | Component (B) | (A)/(B) by weight | Amount of composition added (p.p.m.) | Number of fungi (fungi/g.) |
|---|---|---|---|---|---|
| citrinum | | glycine | 95/5 | 500 | $4 \times 10$ |
| | | | 95/5 | 1000 | 0 |
| | | | 90/10 | 500 | $3 \times 10$ |
| | | | 90/10 | 1000 | 0 |
| | | | 80/20 | 500 | $3 \times 10$ |
| | | | 80/20 | 1000 | 0 |
| | | | 60/40 | 500 | $2 \times 10$ |
| | | | 60/40 | 1000 | 0 |
| | | | 100/0 | 500 | $7 \times 10^7$ |
| | | | 100/0 | 1000 | $40 \times 10^5$ |
| | | | 0/100 | 25 | $5 \times 10^7$ |
| | | | 0/100 | 50 | $8 \times 10^5$ |
| | | | 0/100 | 100 | $30 \times 10^3$ |
| | | | 0/100 | 200 | $6 \times 10$ |
| Penicillium citrinum | Dehydroacetic acid | Sodium salt of 2-pyridinethiol 1-oxide | 99.5/0.5 | 500 | 5 |
| | | | 99.5/0.5 | 1000 | 0 |
| | | | 99/1 | 500 | 0 |
| | | | 99/1 | 1000 | 0 |
| | | | 95/5 | 500 | 2 |
| | | | 95/5 | 1000 | 0 |
| | | | 90/10 | 500 | 0 |
| | | | 80/20 | 500 | 0 |
| | | | 60/40 | 500 | 0 |
| | | | 100/0 | 500 | $1 \times 10^5$ |
| | | | 100/0 | 1000 | $17 \times 10^3$ |
| | | | 0/100 | 5 | $2 \times 10^5$ |
| | | | 0/100 | 10 | $2 \times 10^5$ |
| | | | 0/100 | 25 | $17 \times 10^4$ |
| | | | 0/100 | 50 | $15 \times 10^3$ |
| | | | 0/100 | 100 | $8 \times 10^2$ |
| | | | 0/100 | 200 | $3 \times 10$ |
| Penicillium citrinum | Sorbic acid | Sodium salt of 2-pyridinethiol 1-oxide | 95/5 | 500 | $5 \times 10$ |
| | | | 95/5 | 1000 | 0 |
| | | | 90/10 | 500 | $3 \times 10$ |
| | | | 90/10 | 1000 | 0 |
| | | | 80/20 | 500 | 0 |
| | | | 60/40 | 500 | 0 |
| | | | 100/0 | 500 | $7 \times 10^7$ |
| | | | 100/0 | 1000 | $40 \times 10^5$ |
| | | | 0/100 | 25 | $17 \times 10^4$ |
| | | | 0/100 | 50 | $15 \times 10^3$ |
| | | | 0/100 | 100 | $8 \times 10^2$ |
| | | | 0/100 | 200 | $3 \times 10$ |
| Cladosporium resinae | Dehydroacetic acid | Tetrahydro-3,5-dimethyl-2H-1,3,5-thiadiazine-2-thione | 95/5 | 100 | $8 \times 10$ |
| | | | 95/5 | 500 | 0 |
| | | | 90/10 | 100 | $5 \times 10$ |
| | | | 90/10 | 500 | 0 |
| | | | 80/20 | 100 | 9 |
| | | | 80/20 | 500 | 0 |
| | | | 60/40 | 100 | 0 |
| | | | 100/0 | 100 | $15 \times 10^7$ |
| | | | 100/0 | 500 | $10 \times 10^5$ |
| | | | 0/100 | 5 | $27 \times 10^5$ |
| | | | 0/100 | 25 | $11 \times 10^3$ |
| | | | 0/100 | 50 | $11 \times 10^2$ |
| | | | 0/100 | 100 | $9 \times 10$ |
| Cladosporium resinae | Sorbic acid | Tetrahydro-3,5-dimethyl-2H-1,3,5-thiadiazine-2-thione | 95/5 | 100 | $7 \times 10$ |
| | | | 95/5 | 500 | 2 |
| | | | 90/10 | 100 | 6 |
| | | | 80/20 | 500 | 0 |
| | | | 80/20 | 100 | 0 |
| | | | 60/40 | 100 | 0 |
| | | | 100/0 | 100 | $9 \times 10^7$ |
| | | | 100/0 | 500 | $15 \times 10^6$ |
| | | | 0/100 | 5 | $27 \times 10^5$ |
| | | | 0/100 | 25 | $11 \times 10^3$ |
| | | | 0/100 | 50 | $11 \times 10^2$ |
| | | | 0/100 | 100 | $9 \times 10$ |

EXAMPLE 3

A 10% aqueous solution of a polyvinyl alcohol sizing agent was prepared and divided into three portions. To the first portion was added no medicine, to the second portion was added 2,000 p.p.m. of sodium dehydroacetate, and to the third portion were added 1,000 p.p.m. of sodium dehydroacetate and 100 p.p.m. of dodecyldi(aminoethyl)-glycine. Epicoccum sp. was inoculated to each of three portions, and they were allowed to stand in an incubator at 30° C. for 14 days.

In the first and second portions, development of fungi was observed after 3 and 5 days, respectively, but in the third portion no development of fungi was observed.

The coated fancy mats were allowed to stand under a saturated humidity at 25° C., and the state of the growth of fungi was observed with the lapse of time.

The results are shown in Table 3, in which symbols are as follows:

−: No growth
±: A little growth
+: Growth (The more the number of the symbol +, the larger the growth).

TABLE 3

| Amount of composition (p.p.m.) | Incubation days | | | | | | |
|---|---|---|---|---|---|---|---|
| | 5 | 6 | 7 | 8 | 10 | 12 | 14 |
| 0 | − | + | ++ | +++ | ++++ | +++++ | +++++ |
| 2,500 | − | − | + | + | +++ | +++ | ++++ |
| 5,000 | − | − | − | ± | + | ++ | +++ |
| 7,500 | − | − | − | − | − | − | − |

EXAMPLE 4

The procedure of Example 3 was repeated except that potassium sorbate was employed instead of sodium dehydroacetate.

In the first and second portions, development of fungi was observed after 4 and 6 days, respectively, but in the third portion no development of fungi was observed.

EXAMPLE 5

The procedure of Example 3 was repeated except that tetradecyldi(aminoethyl)glycine was employed instead of dodecyldi(aminoethyl)glycine.

In the first and second portions, development of fungi was observed after 3 and 5 days, respectively, but in the third portions no development of fungi was observed.

EXAMPLE 7

A sizing solution containing 5% of wheat starch and a sizing solution containing 5% of casein were prepared, and thereto was added a medicine as shown in Table 4. After adding a suspension of fungi consisting of Aspergillus niger, Penicillium citrinum, Cladosporium herbaum and Chaetomium globorum to each of the sizing solution, the sizing solutions were placed in an incubator at 28° C. and the state of the growth of fungi was observed.

The results are shown in Table 4, in which symbols are as follows:

−: No growth ±: A little growth
+: Growth (The more the number of the symbol +, the larger the growth).

TABLE 4

| Sizing solution | Medicine | Incubation days | | | | | |
|---|---|---|---|---|---|---|---|
| | | 0 | 4 | 7 | 14 | 21 | 28 |
| Wheat starch | None | − | + | +++ | ++++ | ++++ | ++++ |
| Casein | " | − | − | ++ | +++ | ++++ | ++++ |
| Wheat starch | Sodium dehydroacetate (500 p.p.m.) | − | − | ± | ++ | +++ | +++ |
| Casein | Sodium dehydroacetate (500 p.p.m.) | − | − | − | ± | ++ | +++ |
| Wheat starch | Sodium dehydroacetate (475 p.p.m.) and docecyldi(aminoethyl)glycine (25 p.p.m.) | − | − | − | − | − | − |
| Casein | Sodium dehydroacetate (475 p.p.m.) and dodecyldi(aminoethyl)glycine (25 p.p.m.) | − | − | − | − | − | − |

EXAMPLE 6

An antibacterial, antifungal composition was prepared by admixing 95 g. of sodium dehydroacetate and 5 g. of dodecyldi(aminoethyl)glycine. The composition was added to a 18% solution of a crotonic acid-vinyl acetate copolymer in a concentration of 2,500 p.p.m., 5,000 p.p.m. or 7,500 p.p.m., respectively.

Each of the thus prepared three coating solutions was sprayed onto two sides of a fancy mat (10×10 cm.) in an amount of 2 g. on each side, and was then dried at 140° C. for 2 minutes.

EXAMPLE 8

A 10% aqueous solution of a polyvinyl alcohol sizing agent was prepared and divided into three portions. To the first portion was added no medicine, to the second portion was added 1,000 p.p.m. of sodium dehydroacetate, and to the third portion were added 250 p.p.m. of sodium dehydroacetate and 10 p.p.m. of sodium salt of 2-pyridinethiol 1-oxide. An aqueous suspension of fungi consisting of Epicoccum sp., Cephalosporium sp. and Fusarium oxysporium was added to each of three portions in an amount of 0.3 ml. to 100 g. of the 10% aqueous solution of the sizing agent, and they were then allowed to stand in an incubator at 30° C. for 14 days.

In the first and second portions, development of fungi was observed after 2 and 5 days, respectively, but in the third portion no development of fungi was observed.

EXAMPLE 9

The procedure of Example 8 was repeated except that sodium sorbate was employed instead of sodium dehydroacetate.

In the first and second portions, development of fungi was observed after 3 and 5 days, respectively, but in the third portion no development of fungi was observed.

EXAMPLE 10

Three samples were prepared by admixing 8 ml. of water with each of sample A (5 g. of a mosquito-repellent incense powder containing no medicine), sample B (5 g. of a mosquito-repellent incense powder containing 500 p.p.m. of sodium dehydroacetate) and sample C (5 g. of a mosquito-repellent incense powder containing 250 p.p.m. of sodium dehydroacetate and 10 p.p.m. of sodium salt of 2-pyridinethiol 1-oxide) and then molding the resulting mixture into a disc having a radius of 5 cm. and a thickness of 0.5 cm. To each sample was added 0.3 ml. of an aqueous suspension of fungi consisting of *Aspergillus niger, Penicillium luteum, Cladosporium herbaum, Pullularia pullulans* and *Fusarium oxyporium*.

The samples were allowed to stand at a temperature of 28° C. and a humidity of 90% for two weeks, and the state of the development of fungi was then observed.

In sample A and sample B, development of fungi was observed after 2 and 5 days, respectively, but in sample C no development of fungi was observed.

EXAMPLE 11

To a polyvinyl acetate emulsion (solid content: 10%) was added 2% of agar, and by employing this emulsion the following three samples were prepared; sample A: emulsion containing no medicine, sample B: emulsion containing 1,000 p.p.m. of sodium dehydroacetate, and sample C: emulsion containing 250 p.p.m. of sodium dehydroacetate and 10 p.p.m. of sodium salt of 2-pyridinethiol 1-oxide.

An aqueous suspension of fungi of *Aspergillus niger* was added dropwise to each sample, and was cultured in an incubator at 28° C.

In sample A and sample B, development of fungi was observed after 2 and 5 days, respectively, but in sample C no development of fungi was observed even after a week.

EXAMPLE 12

By employing a sizing solution containing 5% of wheat starch, the following three samples were prepared; sample A: sizing solution containing no medicine, sample B: sizing solution containing 500 p.p.m. of sodium dehydroacetate, and sample C: sizing solution containing 100 p.p.m. of sodium dehydroacetate and 50 p.p.m. of 2-pyridinethiol 1-oxide. An aqueous suspension of fungi consisting of *Aspergillus niger, Penicillium citrinum, Cladosporium herbaum* and *Chaetomium globosum* was inoculated into each sample, and the state of the development of fungi was observed in an incubator at 28° C.

In sample A and sample B, development of fungi was observed after 2 and 4 days, respectively, but in sample C no development of fungi was observed even after 21 days.

EXAMPLE 13

By employing a wall covering material for decorative use (commercially available under the tradename "Orion Coat Kabe" made by Umehiko Co.), the following three samples were prepared; sample A: wall covering material containing no medicine, sample B: wall covering material containing 0.1% of sodium dehydroacetate, and sample C: wall covering material containing 0.09% of sodium dehydroacetate and 0.01% of sodium salt of 2-pyridinethiol 1-oxide. Each sample was thoroughly admixed with water and was coated thin on a veneer. After air-dry for 2 days, the coated veneers were cut into pieces of 5 cm.×5 cm. and the coatings were then peeled off.

A drop of an aqueous suspension of *Aspergillus niger* was dropped on each coating, and the state of the development of fungi was observed at a temperature of 28° C. and a humidity of 91%.

In sample A and sample B, development of fungi was observed after 2 and 3 days, respectively, but in sample C no development of fungi was observed after the lapse of at least a week.

EXAMPLE 14

To 99 g. of a water base putty were added an antibacterial, antifungal composition consisting of the components (A) and (B) as shown in Table 5 and 1 ml. of an aqueous suspension of bacteria and fungi (bacteria: *Pseudomonas aeruginosa, Escherichia coli, Bacillus subtilis* and *Staphylococcus aureus*, fungi: *Aspergillus niger, Aspergillus oryzae, Cladosporium resinae, Cheatomium globosum* and *Penicillium citrinum*), and they were thoroughly admixed. The thus prepared sample contained bacteria of $15 \times 10^6$ cells/g. and fungi of $6 \times 10^5$ cells/g.

The sample was placed in a bottle, and after sealing the bottle, the bottle was placed in an incubator at 30° C. and the state of the growth of microorganisms was observed with the lapse of time. The state of the growth was evaluated by measuring the number of bacteria and fungi in 1 g. of the sample.

The results are shown in Table 5.

TABLE 5

| Antibacterial, antifungal composition | | | Content of composition in sample (%) | Number of microorganism (cells/g.) | | | |
|---|---|---|---|---|---|---|---|
| | | | | After 10 days | | After 30 days | |
| Component (A) | Component (B) | (A)/(B) by weight | | Bacteria | Fungi | Bacteria | Fungi |
| Potassium sorbate | Tetrahydro-3,5-dimethyl-2H-1,3,5-thiadiazine-2-thione | 95/5 | 0.02 | $13 \times 10^2$ | 0 | $7 \times 10^2$ | 0 |
| | | 95/5 | 0.05 | 0 | 0 | 0 | 0 |
| | | 80/20 | 0.02 | $10 \times 10^2$ | 0 | $3 \times 10^2$ | 0 |
| | | 80/20 | 0.05 | 0 | 0 | 0 | 0 |
| | | 100/0 | 0.05 | $25 \times 10^6$ | $9 \times 10^5$ | $18 \times 10^8$ | $11 \times 10^7$ |
| | | 0/100 | 0.01 | $16 \times 10^4$ | $3 \times 10^5$ | $34 \times 10^4$ | $5 \times 10^5$ |

TABLE 5-continued

| Antibacterial, antifungal composition | | | Content of composition in sample (%) | Number of microorganism (cells/g.) | | | |
|---|---|---|---|---|---|---|---|
| | | | | After 10 days | | After 30 days | |
| Component (A) | Component (B) | (A)/(B) by weight | | Bacteria | Fungi | Bacteria | Fungi |
| Sodium dehydro-acetate | Tetrahydro-3,5-dimethyl-2H-1,3,5-thiadi-azine-2-thione | 95/5 | 0.02 | $14 \times 10^2$ | 0 | $5 \times 10^2$ | 0 |
| | | 95/5 | 0.05 | 0 | 0 | 0 | 0 |
| | | 80/20 | 0.02 | $8 \times 10^2$ | 0 | 0 | 0 |
| | | 80/20 | 0.05 | 0 | 0 | 0 | 0 |
| | | 100/0 | 0.05 | $18 \times 10^6$ | $12 \times 10^4$ | $27 \times 10^8$ | $13 \times 10^4$ |
| | | 0/100 | 0.01 | $16 \times 10^4$ | $3 \times 10^5$ | $34 \times 10^4$ | $5 \times 10^5$ |
| Sorbic acid | Tetrahydro-3,5-dimethyl-2H-1,3,5-thiadi-azine-2-thione | 95/5 | 0.02 | $13 \times 10^2$ | 0 | $6 \times 10^2$ | 0 |
| | | 95/5 | 0.05 | 0 | 0 | 0 | 0 |
| | | 80/20 | 0.02 | $9 \times 10^2$ | 0 | $2 \times 10^2$ | 0 |
| | | 80/20 | 0.05 | 0 | 0 | 0 | 0 |
| | | 100/0 | 0.05 | $23 \times 10^6$ | $15 \times 10^5$ | $8 \times 10^8$ | $22 \times 10^7$ |
| | | 0/100 | 0.01 | $16 \times 10^4$ | $3 \times 10^5$ | $34 \times 10^4$ | $5 \times 10^5$ |
| Dehydroacetic acid | Tetrahydro-3,5-dimethyl-2H-1,3,5-thiadi-azine-2-thione | 95/5 | 0.02 | $3 \times 10^2$ | 0 | $3 \times 10^2$ | 0 |
| | | 95/5 | 0.05 | 0 | 0 | 0 | 0 |
| | | 80/20 | 0.02 | $2 \times 10^2$ | 0 | 0 | 0 |
| | | 80/20 | 0.05 | 0 | 0 | 0 | 0 |
| | | 100/0 | 0.05 | $15 \times 10^6$ | $7 \times 10^4$ | $14 \times 10^8$ | $7 \times 10^4$ |
| | | 0/100 | 0.01 | $16 \times 10^4$ | $3 \times 10^5$ | $34 \times 10^4$ | $5 \times 10^5$ |
| — | — | — | 0 | $12 \times 10^8$ | $>10^{10}$ | $25 \times 10^8$ | $>10^{10}$ |

EXAMPLE 15

The procedures of Example 14 were repeated except a polyvinyl acetate emulsion was employed instead of the putty and a sample emulsion containing bacteria of $25 \times 10^5$ cells/g. and fungi of $13 \times 10^5$ cells/g. was prepared.

The results are shown in Table 6.

TABLE 6

| Antibacterial, antifungal composition | | | Content of composition in emulsion (%) | Number of microorganism (cells/g.) | | | | | |
|---|---|---|---|---|---|---|---|---|---|
| | | | | After 1 month | | After 2 months | | After 3 months | |
| Component (A) | Composition (B) | (A)/(B) by wt. | | Bacteria | Fungi | Bacteria | Fungi | Bacteria | Fungi |
| Potassium sorbate | Tetrahydro-3,5-dimethyl-2H-1,3,5-thiadi-azine-2-thione | 95/5 | 0.05 | $3 \times 10^2$ | $3 \times 10^2$ | 0 | 0 | 0 | 0 |
| | | 95/5 | 0.1 | $2 \times 10^2$ | 0 | 0 | 0 | 0 | 0 |
| | | 80/20 | 0.05 | $4 \times 10^2$ | $5 \times 10^2$ | 0 | 0 | 0 | 0 |
| | | 80/20 | 0.1 | $3 \times 10^2$ | 0 | 0 | 0 | 0 | 0 |
| | | 100/0 | 0.1 | $23 \times 10^5$ | $9 \times 10^5$ | $18 \times 10^7$ | $8 \times 10^8$ | $15 \times 10^8$ | $>10^{10}$ |
| | | 0/100 | 0.02 | $18 \times 10^4$ | $21 \times 10^4$ | $6 \times 10^5$ | $31 \times 10^4$ | $5 \times 10^5$ | $26 \times 10^4$ |
| Sodium dehydroacetate | Tetrahydro-3,5-dimethyl-2H-1,3,5-thiadi-azine-2-thione | 95/5 | 0.05 | $18 \times 10^2$ | $21 \times 10^2$ | $2 \times 10^2$ | $3 \times 10^2$ | 0 | 0 |
| | | 95/5 | 0.1 | $2 \times 10^2$ | $2 \times 10^2$ | 0 | 0 | 0 | 0 |
| | | 80/20 | 0.05 | $4 \times 10^2$ | 0 | 0 | 0 | 0 | 0 |
| | | 80/20 | 0.1 | $3 \times 10^2$ | 0 | 0 | 0 | 0 | 0 |
| | | 100/0 | 0.1 | $14 \times 10^5$ | $5 \times 10^4$ | $9 \times 10^6$ | $13 \times 10^4$ | $32 \times 10^8$ | $>10^{10}$ |
| | | 0/100 | 0.2 | $18 \times 10^4$ | $21 \times 10^4$ | $6 \times 10^5$ | $31 \times 10^4$ | $5 \times 10^5$ | $26 \times 10^4$ |
| Sorbic acid | Tetrahydro-3,5-dimethyl-2H-1,3,5-thiadi-azine-2-thione | 95/5 | 0.05 | $2 \times 10^2$ | 0 | 0 | 0 | 0 | 0 |
| | | 95/5 | 0.1 | $1 \times 10^2$ | 0 | 0 | 0 | 0 | 0 |
| | | 80/20 | 0.05 | $11 \times 10^2$ | 0 | 0 | 0 | 0 | 0 |
| | | 80/20 | 0.1 | $7 \times 10^2$ | 0 | 0 | 0 | 0 | 0 |
| | | 100/0 | 0.1 | $18 \times 10^5$ | $5 \times 10^5$ | $15 \times 10^7$ | $>10^{10}$ | $9 \times 10^8$ | $>10^{10}$ |
| | | 0/100 | 0.02 | $18 \times 10^4$ | $21 \times 10^4$ | $6 \times 10^5$ | $31 \times 10^4$ | $5 \times 10^5$ | $26 \times 10^4$ |
| Dehydro-acetic acid | Tetrahydro-3,5-dimethyl-2H-1,3,5-thiadi-azine-2-thione | 95/5 | 0.05 | $6 \times 10^2$ | $1 \times 10^2$ | 0 | 0 | 0 | 0 |
| | | 95/5 | 0.1 | $5 \times 10^2$ | 0 | 0 | 0 | 0 | 0 |
| | | 80/20 | 0.05 | $2 \times 10^2$ | $2 \times 10^2$ | 0 | 0 | 0 | 0 |
| | | 80/20 | 0.1 | $2 \times 10^2$ | 0 | 0 | 0 | 0 | 0 |
| | | 100/0 | 0.1 | $14 \times 10^5$ | $3 \times 10^4$ | $16 \times 10^6$ | $13 \times 10^5$ | $21 \times 10^8$ | $>10^{10}$ |
| | | 0/100 | 0.02 | $18 \times 10^4$ | $21 \times 10^4$ | $6 \times 10^5$ | $31 \times 10^4$ | $5 \times 10^5$ | $26 \times 10^4$ |
| — | — | — | 0 | $33 \times 10^6$ | $19 \times 10^6$ | $19 \times 10^8$ | $>10^{10}$ | $20 \times 10^8$ | $>10^{10}$ |

What we claim is:

1. An antibacterial and antifungal composition comprising a mixture of (A) 60% to 99.5% by weight, based on the total weight of the composition, of at least one member selected from the group consisting of dehydroacetic acid and its alkali metal salts and (B) 0.5% to 40% by weight, based on the total weight of the composition, of at least one member selected from the group consisting of 2-pyridinethiol 1-oxide and its salts.

2. An antibacterial and antifungal composition comprising a mixture of (A) at least one member selected from the group consisting of dehydroacetic acid and its alkali metal salts and (B) at least one member selected from the group consisting of 2-pyridinethiol 1-oxide and its salts, the weight ratio of (A) to (B) being in the range of 99.5/0.5 to 60/40.

* * * * *